US007004954B1

(12) United States Patent
Voss et al.

(10) Patent No.: US 7,004,954 B1
(45) Date of Patent: *Feb. 28, 2006

(54) DEVICE FOR REMOVAL OF THROMBUS THROUGH PHYSIOLOGICAL ADHESION

(75) Inventors: Larry Voss, San Jose, CA (US); William Stephen Tremulis, Redwood City, CA (US)

(73) Assignee: Endovascular Technologies, Inc., Santa Clara, CA (US)

(*) Notice: Subject to any disclaimer, the term of this patent is extended or adjusted under 35 U.S.C. 154(b) by 62 days.

This patent is subject to a terminal disclaimer.

(21) Appl. No.: 10/326,720

(22) Filed: Dec. 19, 2002

Related U.S. Application Data

(63) Continuation of application No. 09/532,629, filed on Mar. 22, 2000, now Pat. No. 6,514,273.

(51) Int. Cl.
*A61M 29/00* (2006.01)
(52) U.S. Cl. ..................... 606/200; 606/127
(58) Field of Classification Search ............... 606/200, 606/113, 127, 108
See application file for complete search history.

(56) References Cited

U.S. PATENT DOCUMENTS

| 2,943,626 A | 7/1960 | Dormia |
| 3,472,230 A | 10/1969 | Fogarty |
| 3,635,223 A | 1/1972 | Klieman |
| 3,868,956 A | 3/1975 | Alfidi |
| 3,978,863 A | 9/1976 | Fettel |
| 3,996,938 A | 12/1976 | Clark, III |
| 4,030,503 A | 6/1977 | Clark, III |
| 4,611,594 A | 9/1986 | Grayhack et al. |
| 4,612,931 A | 9/1986 | Dormia |
| 4,619,246 A | 10/1986 | Molgaard-Nielsen |
| 4,643,184 A | 2/1987 | Mobin-Uddin |
| 4,646,736 A | 3/1987 | Auth |
| 4,650,466 A | 3/1987 | Luther |
| 4,706,671 A | 11/1987 | Weinrib |
| 4,727,873 A | 3/1988 | Mobin-Uddin |
| 4,762,130 A | 8/1988 | Fogarty |
| 4,790,812 A | 12/1988 | Hawkins, Jr. |
| 4,832,055 A | 5/1989 | Palestrant |
| 4,865,017 A | 9/1989 | Shinozuka |
| 4,873,978 A | 10/1989 | Ginsburg |
| 4,885,003 A | 12/1989 | Hillstead |
| 4,890,611 A | 1/1990 | Monfort et al. |
| 4,921,484 A | 5/1990 | Hillstead |
| 4,926,858 A | 5/1990 | Gifford, III |
| 4,969,891 A | 11/1990 | Gewertz |
| 4,997,435 A | 3/1991 | Demeter |
| 4,998,539 A | 3/1991 | Delsanti |
| 5,011,488 A | 4/1991 | Ginsburg |
| 5,034,001 A | 7/1991 | Garrison et al. |
| 5,041,093 A | 8/1991 | Chu |
| 5,047,040 A | 9/1991 | Simpson |
| 5,053,008 A | 10/1991 | Bajaj |

(Continued)

FOREIGN PATENT DOCUMENTS

EP 0 418 677 3/1991

(Continued)

*Primary Examiner*—(Jackie) Tan-Uyen T. Ho
(74) *Attorney, Agent, or Firm*—Fulwider Patton LLP

(57) ABSTRACT

A device that is useful for removing obstructions from vessels. Various embodiments and methods of use are contemplated for the effective removal of obstructions. The disclosed devices utilize a thrombogenic material to promote the formation of fibrin bonds, thus enhancing adhesion. It is further contemplated that the disclosed devices may be used in all vasculature including the cerebral vasculature and the neurovasculature.

9 Claims, 4 Drawing Sheets

U.S. PATENT DOCUMENTS

| | | |
|---|---|---|
| 5,057,114 A | 10/1991 | Wittich et al. |
| 5,064,428 A | 11/1991 | Cope |
| 5,092,839 A | 3/1992 | Kipperman |
| 5,100,423 A | 3/1992 | Fearnot |
| 5,102,415 A | 4/1992 | Guenther |
| 5,112,347 A | 5/1992 | Taheri |
| 5,133,733 A | 7/1992 | Rasmussen |
| 5,152,777 A | 10/1992 | Goldberg |
| 5,171,233 A | 12/1992 | Amplatz et al. |
| 5,180,368 A | 1/1993 | Garrison |
| 5,190,557 A | 3/1993 | Borodulin |
| 5,192,286 A | 3/1993 | Phan |
| 5,192,290 A | 3/1993 | Hilal |
| 5,221,261 A | 6/1993 | Termin et al. |
| 5,222,971 A | 6/1993 | Willard |
| 5,324,304 A | 6/1994 | Rasmussen |
| 5,329,942 A | 7/1994 | Gunther |
| 5,330,482 A | 7/1994 | Gibbs |
| 5,330,484 A | 7/1994 | Gunther et al. |
| 5,354,310 A | 10/1994 | Garnic et al. |
| 5,370,653 A | 12/1994 | Cragg |
| 5,411,509 A | 5/1995 | Hilal |
| 5,421,832 A | 6/1995 | Lefebvre |
| 5,449,372 A | 9/1995 | Schmaltz |
| 5,490,859 A | 2/1996 | Mische |
| 5,496,277 A | 3/1996 | Termin et al. |
| 5,496,330 A | 3/1996 | Bates |
| 5,501,694 A | 3/1996 | Ressemann |
| 5,509,923 A | 4/1996 | Middleman et al. |
| 5,522,825 A | 6/1996 | Kropf |
| 5,527,282 A | 6/1996 | Segal |
| 5,527,326 A | 6/1996 | Hermann et al. |
| 5,540,707 A | 7/1996 | Ressemann et al. |
| 5,549,626 A | 8/1996 | Miller |
| 5,607,466 A | 3/1997 | Imbert |
| 5,626,602 A | 5/1997 | Gianotti et al. |
| 5,649,906 A | 7/1997 | Gory et al. |
| 5,669,933 A | 9/1997 | Simon et al. |
| 5,688,234 A | 11/1997 | Frisbie |
| 5,695,469 A | 12/1997 | Segal |
| 5,695,507 A | 12/1997 | Auth et al. |
| 5,695,518 A | 12/1997 | Laerum |
| 5,695,519 A | 12/1997 | Summers et al. |
| 5,702,413 A | 12/1997 | Lafontaine |
| 5,713,853 A | 2/1998 | Clark et al. |
| 5,720,754 A | 2/1998 | Middleman et al. |
| 5,720,764 A | 2/1998 | Naderlinger |
| 5,725,571 A | 3/1998 | Imbert |
| 5,746,767 A | 5/1998 | Smith |
| 5,749,883 A | 5/1998 | Halpern |
| 5,755,790 A | 5/1998 | Chevillon et al. |
| 5,766,191 A | 6/1998 | Trerotola |
| 5,769,816 A | 6/1998 | Barbut et al. |
| 5,769,871 A | 6/1998 | Mers Kelly et al. |
| 5,772,674 A | 6/1998 | Nakhjavan |
| 5,792,145 A | 8/1998 | Bates et al. |
| 5,792,156 A | 8/1998 | Perouse |
| 5,792,157 A | 8/1998 | Mische |
| 5,795,322 A | 8/1998 | Boudewijn |
| 5,800,454 A | 9/1998 | Jacobsen et al. |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,304 A | 10/1998 | Hart |
| 5,827,324 A | 10/1998 | Cassell |
| 5,836,868 A | 11/1998 | Ressemann |
| 5,846,251 A | 12/1998 | Hart |
| 5,848,964 A | 12/1998 | Samuels |
| 5,868,708 A | 2/1999 | Hart |
| 5,868,754 A | 2/1999 | Levine |
| 5,876,367 A | 3/1999 | Kaganov et al. |
| 5,882,329 A | 3/1999 | Patterson et al. |
| 5,893,869 A | 4/1999 | Barnhart et al. |
| 5,895,398 A | 4/1999 | Wensel et al. |
| 5,895,400 A | 4/1999 | Abela |
| 5,895,410 A | 4/1999 | Forber et al. |
| 5,897,567 A | 4/1999 | Ressemann et al. |
| 5,902,263 A | 5/1999 | Patterson et al. |
| 5,904,690 A | 5/1999 | Middleman et al. |
| 5,908,435 A | 6/1999 | Samuels |
| 5,910,154 A | 6/1999 | Tsugita et al. |
| 5,911,717 A | 6/1999 | Jacobsen et al. |
| 5,911,734 A | 6/1999 | Tsugita et al. |
| 5,928,261 A | 7/1999 | Ruiz |
| 5,935,139 A | 8/1999 | Bates |
| 6,010,517 A | 1/2000 | Baccaro |
| 6,053,932 A | 4/2000 | Daniel |
| 6,168,603 B1 | 1/2001 | Leslie et al. |
| 6,168,622 B1 | 1/2001 | Mazzocchi |
| 6,238,403 B1 | 5/2001 | Greene et al. |
| 6,238,412 B1 | 5/2001 | Dubrul et al. |

FOREIGN PATENT DOCUMENTS

| | | |
|---|---|---|
| EP | 0 472 368 | 6/1995 |
| JP | HEI 10 (1998)-151136 | 6/1998 |
| WO | WO 94/24946 | 11/1994 |
| WO | WO 96/01591 | 1/1996 |

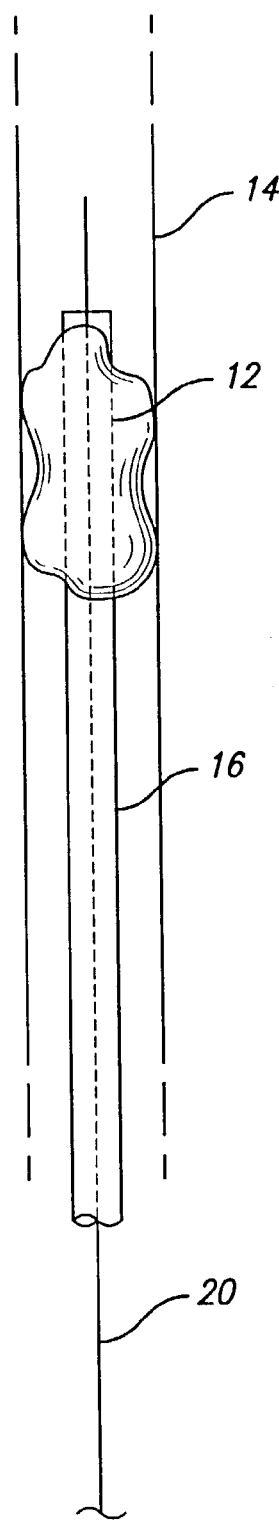
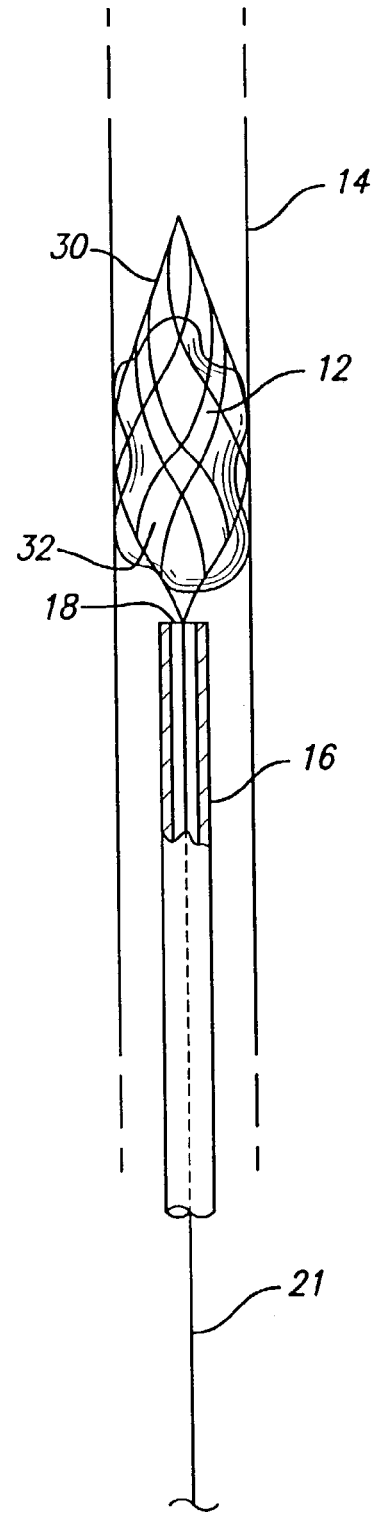
FIG. 3
FIG. 4

DEVICE FOR REMOVAL OF THROMBUS THROUGH PHYSIOLOGICAL ADHESION

CROSS-REFERENCE TO RELATED APPLICATIONS

This is a continuation of U.S. Ser. No. 09/532,629, filed Mar. 22, 2000 now U.S. Pat. No. 6,514,273. Each of these applications are assigned to the assignee of the present application and are incorporated herein by reference.

BACKGROUND OF THE INVENTION

This invention relates generally to medical devices used during vascular intervention, and more particularly, concerns medical devices that are useful in treating thromboembolic disorders and for removal of foreign bodies in the vascular system.

Thromboembolic disorders, such as stroke, pulmonary embolism, peripheral thrombosis, atherosclerosis, and the like, affect many people. These disorders are a major cause of morbidity and mortality in the United States and throughout the world. Thromboembolic events are characterized by an occlusion of a blood vessel. The occlusion is caused by a clot which is viscoelastic (jelly-like) and is comprised of platelets, fibrinogen, and other clotting proteins.

When an artery is occluded by a clot, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

There are many existing techniques employed to reestablish blood flow in an occluded vessel. One common surgical technique, an embolectomy, involves incising a blood vessel and introducing a balloon-tipped device (such as the Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to such surgery may be traumatic and is best avoided when possible. Additionally, the use of a Fogarty catheter may be problematic due to the possible risk of damaging the interior lining of the vessel as the catheter is being withdrawn. Further, the balloon of the Fogarty catheter may not successfully retain all of the obstruction when pulled through the tortuous vasculature.

Percutaneous methods are also utilized for reestablishing blood flow. A common percutaneous technique is referred to as balloon angioplasty where a balloon-tipped catheter is introduced into a blood vessel, typically through an introducing catheter. The balloon-tipped catheter is then advanced to the point of the occlusion and inflated in order to dilate the stenosis. Balloon angioplasty is appropriate for treating vessel stenosis but is generally not effective for treating acute thromboembolisms.

Another percutaneous technique is to place a microcatheter near the clot and infuse Streptokinase, Urokinase, or other thrombolytic agents to dissolve the clot. Unfortunately, thrombolysis typically takes hours to days to be successful. Additionally, thrombolytic agents can cause hemorrhage and in many patients the agents cannot be used at all.

Another problematic area is the removal of foreign bodies. Foreign bodies introduced into the circulation can be fragments of catheters, pace-maker electrodes, guide wires, and erroneously placed embolic material such as thrombogenic coils. There exist retrieval devices for the removal of foreign bodies, certain of such devices forming a loop that can ensnare the foreign material by decreasing the size of the diameter of the loop around the foreign body. The use of some such removal devices can be difficult and sometimes unsuccessful. For example, some of these devices may fail to completely capture the obstruction.

Various thrombectomy and foreign matter removal devices have been disclosed in the art. However, such devices have been found to have structures that are either highly complex or lacking in sufficient retaining structure. Disadvantages associated with the devices having highly complex structure include difficulty in manufacturability as well as use in conjunction with microcatheters. Other less complex devices tend to pull through clots, due in part to the lack of experience in using the same, or are otherwise inadequate in capturing clots or foreign bodies. Additionally, many of the prior art thrombectomy devices carry with them a significant risk of producing distal embolization as a thrombus is disrupted. It would be desirable to provide for the quick removal of a thrombus while still intact, thus restoring native blood flow and minimizing the production of emboli.

Moreover, systems heretofore disclosed in the art are generally limited by size compatibility and the increase in vessel size as the emboli is drawn out from the distal vascular occlusion location to a more proximal location near the heart. If the embolectomy device is too large for the vessel it will not deploy correctly to capture the clot or foreign body, and if too small in diameter it cannot capture clots or foreign bodies across the entire cross section of the blood vessel. Additionally, if the embolectomy device is too small in retaining volume then as the device is retracted the excess material being removed can spill out and be carried by flow back to occlude another distal vessel. These and other problems are solved by the present invention.

What has been needed and heretofore unavailable is an extraction device that can be easily and controllably deployed into the circulatory system for the safe and effective removal of clots and foreign bodies. Moreover, due to difficult-to-access anatomy such as the cerebral vasculature and the neurovasculature the invention should possess a small collapsed profile and preferably be self-expanding to allow the device to be delivered through the lumen of commercially available catheters. It is also important that the system minimize occlusion of the vessel. Notably, the invention should provide an improved level of ability to safely capture clots and foreign material in the blood. The present invention satisfies these needs.

SUMMARY OF THE INVENTION

Briefly, and in general terms, the present invention involves devices that provide an improved level of ability to quickly capture and remove clots and foreign bodies in the blood vessels while they are still intact, thus restoring native blood flow and minimizing the production of emboli. Various embodiments and methods of use are disclosed for the effective removal of clots or foreign bodies. It is contemplated that the present invention may be used in all vasculature including the cerebral vasculature and the neurovasculature.

In one aspect of the invention, there is provided a system for removing an obstruction from a vessel including an elongate tubular member. A wire is provided having one end positionable within the elongate tubular member, wherein the other end is designed to promote bonds to the obstruction, which utilize native blood-borne constituents, thereby creating adhesion to facilitate removal of the obstruction. Consequently, less retaining structure is required and the device can be compressed to a smaller diameter for delivery through the vasculature.

In another aspect of the invention, there is provided a method for removing an obstruction from a vessel that utilizes a system including a member having two ends. The method includes the steps of advancing the system to a treatment site; inserting the distal end of the member into the obstruction, wherein the distal end promotes bonds to the obstruction utilizing blood-borne constituents, thereby creating adhesion to facilitate removal of the obstruction; and removing the obstruction from the vessel.

Other features and advantages of the present invention will become more apparent from the following detailed description of the invention when taken in conjunction with the accompanying exemplary drawings.

BRIEF DESCRIPTION OF THE DRAWINGS

FIG. 3 is a schematic illustration showing the catheter of FIG. 1 inserted through an occlusion;

FIG. 4 shows a schematic illustration depicting the system of FIG. 1 with a capture device deployed;

DESCRIPTION OF THE PREFERRED EMBODIMENTS

Figure 1:
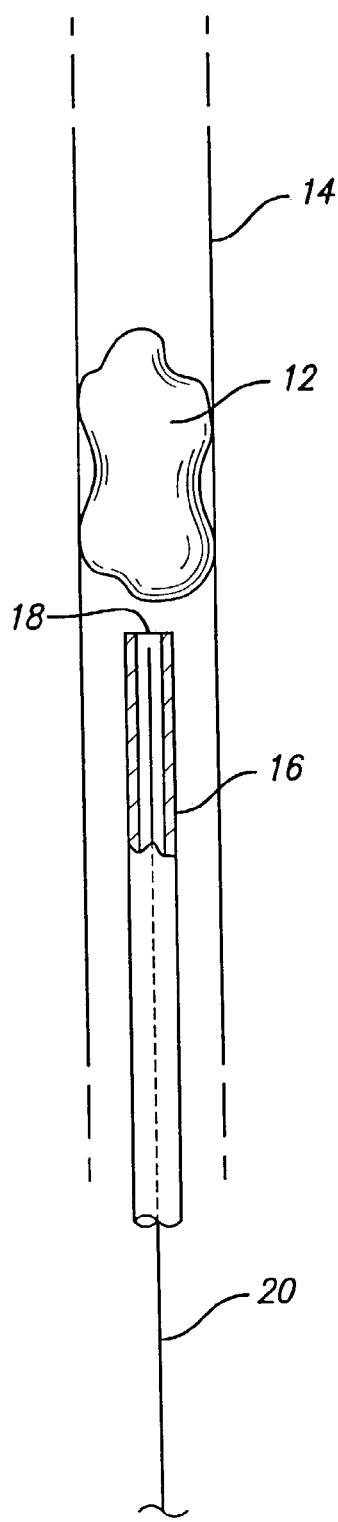
FIG. 1 is a schematic illustration depicting an occluded vessel with a catheter shown partially in cross-section and a first embodiment of the present invention.
Figure 2:
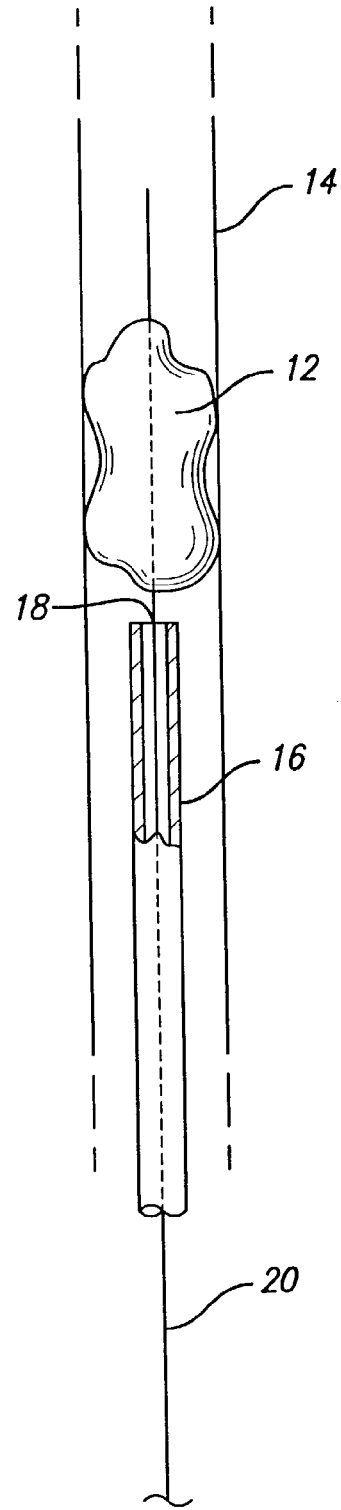
FIG. 2 shows a schematic illustration depicting the wire of FIG. 1 inserted through an occlusion.

As shown in the exemplary drawings wherein like reference numerals indicate like or corresponding elements among the figures, the present invention is embodied in a device for the removal of thrombi through physiological adhesion. The present invention is intended to be used in various sized vessels and in vessels having various degrees of tortuosity. Of particular significance is the contemplated use of the invention in the highly tortuous cerebral vasculature and neurovasculature. Moreover, the disclosed devices are characterized by limiting the risk of producing distal embolization as a thrombus is disrupted. This is accomplished by the quick removal of a thrombus while still intact, thus restoring native blood flow and minimizing the production of emboli.

As mentioned above, it is desirable to have a system that can provide for effective thrombectomy in difficult-to-access anatomy such as the cerebral vasculature and the neurovasculature. Furthermore, the invention should possess a small collapsed profile and preferably be self-deploying to allow the system to be delivered through the lumen of commercially available catheters.

In accordance with the present invention, FIGS. 1–4 depict a first embodiment of a system for removing thrombus 12 from vessel 14. It is contemplated that the present invention can be used to remove other obstructions or foreign materials from a vessel as well. The present invention is especially useful for trapping and removing thrombi from difficult-to-access distal locations within the highly tortuous cerebral vasculature and neurovasculature.

The system includes elongate tubular member 16 having a proximal end and a distal end. The elongate tubular member 16 is preferably a microcatheter or other suitable catheter or tubular device for accessing the vasculature, and especially the cerebral vasculature and the neurovasculature. Microcatheters 16 are known in the art and can be constructed from any appropriate biologically compatible material. Typically, microcatheter 16 will have lumen 18 and will be constructed from a flexible elastomeric material such as silicone, rubber, polyvinyl chloride, polyeurothanes, polyesters, polytetrafluoroethylene, and the like. The microcatheter 16 has to be flexible enough and long enough to navigate through blood vessels to an occluded vessel where thrombi 12 are located. Typically, microcatheter 16 will range in length from approximately 20 to approximately 150 centimeters.

The outer diameter of microcatheter 16 can also vary. Typically, the outer diameter will range from approximately 2 to approximately 10 F (1 F equals 0.013 inch). The inner diameter will range from approximately 1 to approximately 9 F.

Elongate wires 20, 21 are provided each having a proximal end positionable within microcatheter 16 and a distal end. The wires 20, 21 are positionable within lumen 18. The wires 20, 21 may be conventional guide wires or other wire structures, mandrels, or members having similar properties. The wires 20, 21 may be solid or tubular structures. The wires 20, 21 and catheter 16 are useful for navigation through the highly tortuous cerebral vasculature and neurovasculature. One material of choice for wires 20, 21 may be Nitinol. The outer diameter of wires 20, 21 are such that they can easily slide within lumen 18 of catheter 16. Generally, wires 20, 21 each have a length greater than that of the catheter 16 so that their proximal ends can be grasped by an operator and so that wires 20, 21 can be advanced and withdrawn independently of catheter 16.

In keeping with the invention, the distal end of wire 21 preferably includes capture device 30 operatively connected thereto. The capture device 30 may be a self-deploying mesh-like structure constructed of a knitted superelastic wire such as Nitinol, or other metallic, polymeric, or composite materials. The capture device 30 can also be manually-deployable. The capture device 30 can assume both an expanded and a contracted condition. The capture device 30 has a plurality of pores 32. The capture device 30 can be coated with a thrombogenic material such as Thrombin. Alternately, the base material of the device itself may be thrombogenic, or it may be treated in such a way as to make it so, for example, by roughening the surface. It is contemplated that the present invention may take the form of any structure.

In use, wire 20 is inserted into a patient's vasculature using conventional techniques including fluoroscopy or other conventional means. The distal end of wire 20 is advanced within the patient's vasculature and through thrombus 12 to be extracted. Catheter 16 is then advanced over wire 20 and through thrombus 12 so that the distal end of catheter 16 is just protruding from the distal face of thrombus 12. Alternately, catheter 16 can remain close to the proximal face of thrombus 12.

The wire 20 is removed from catheter 16 after the distal end of catheter 16 emerges from the distal face of thrombus 12. The wire 21 is then advanced through catheter 16 and into thrombus 12. The capture device 30 is then deployed from the distal end of catheter 16 so that capture device 30 is in contact with the distal face of thrombus 12 and vessel 14. It is contemplated that capture device 30 can be deployed either within thrombus 12 or just distal to thrombus 12. The capture device 30 can be deployed by withdrawing catheter 16 proximally. Alternatively, capture device 30 can be deployed manually. The mesh-like structure of capture device 30 preferably spans the entire lumen of vessel 14.

The capture device 30 is left in place until new thrombus form around the mesh-like structure on both the proximal and distal faces of thrombus 12. The thrombus 12 and new thrombus hold capture device 30 in its deployed shape. The new thrombus forms a bond via native blood-borne constituents to existing thrombus 12. Adhesion is thereby created to facilitate the removal of thrombus 12. When the new thrombus is sufficiently solidified, capture device 30, catheter 16, and thrombus 12 are withdrawn from the patient's vasculature.

In the event the capture device 30 is treated with thrombogenic material, the same promotes the formation of the fibrin bonds to the thrombus. Generally, fibrin is a white insoluble fibrous protein formed from fibrinogen by the action of thrombin especially in the clotting of blood. Consequently, the thrombogenic material can help solve the problem of a device possessing insufficient retaining structure. Less retaining structure is required, and the device can more easily be compressed and delivered through the vasculature. It is also contemplated that the distal end of one of the wires can be coated with a thrombogenic material, wherein there would be less or no need for a mesh-like structure.

Figure 5:
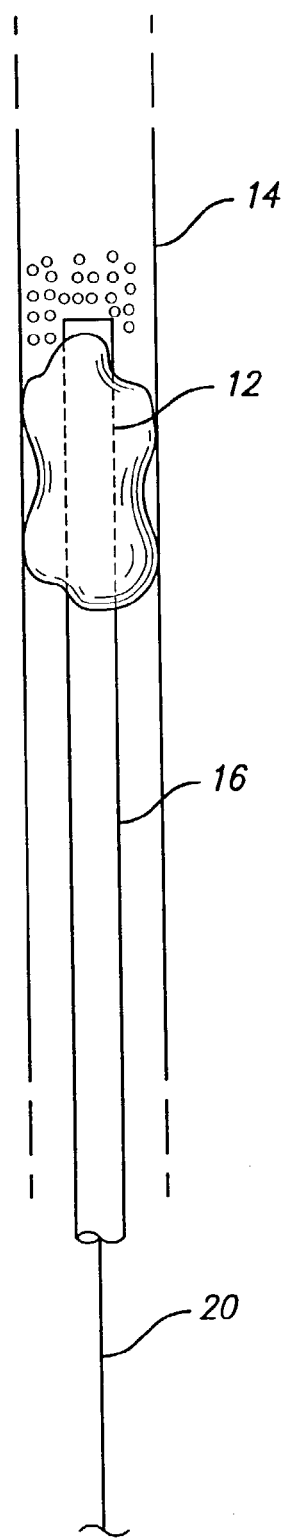
FIG. 5 is a schematic illustration showing a second embodiment of the present invention.

In keeping with the invention, FIG. 5 depicts a second embodiment of the present invention wherein catheter 16 is inserted through thrombus 12. The distal end of catheter 16 is positioned just distal to thrombus 12. The insertion of catheter 16 can be accomplished via the use of a guide wire if so desired. A thrombogenic material is then injected out of the distal end of catheter 16. This promotes thrombus growth, wherein the new thrombus 40 adheres to original thrombus 12. The catheter 16 is slowly withdrawn throughout the length of thrombus 12. Thrombogenic material is continually injected out of the distal end of catheter 16 during this process, until catheter 16 has been withdrawn out of the proximal end of thrombus 12. Consequently, thrombus 12 becomes more solid. The thrombus 12 may then be removed from the patient's vasculature by known methods without the risk of traveling emboli posed to the patient.

Figure 6:
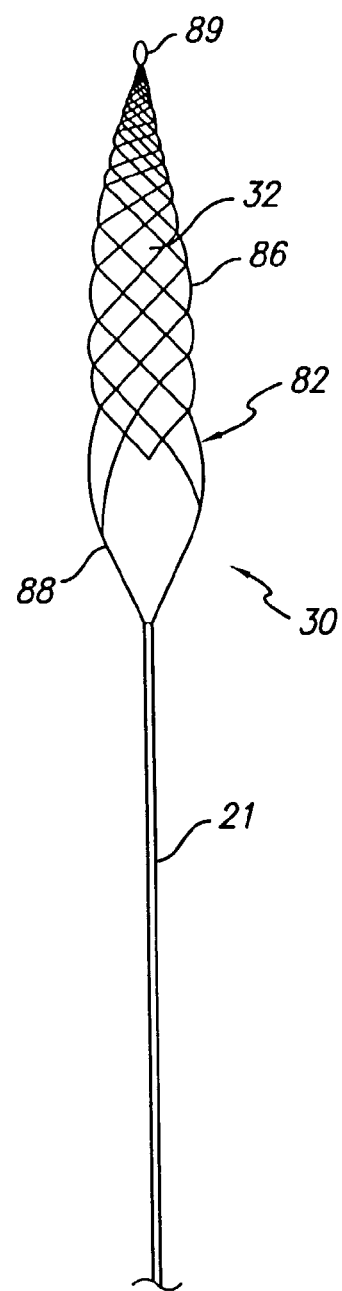
FIG. 6 is a schematic illustration depicting a third embodiment of the present invention.
Figure 7:
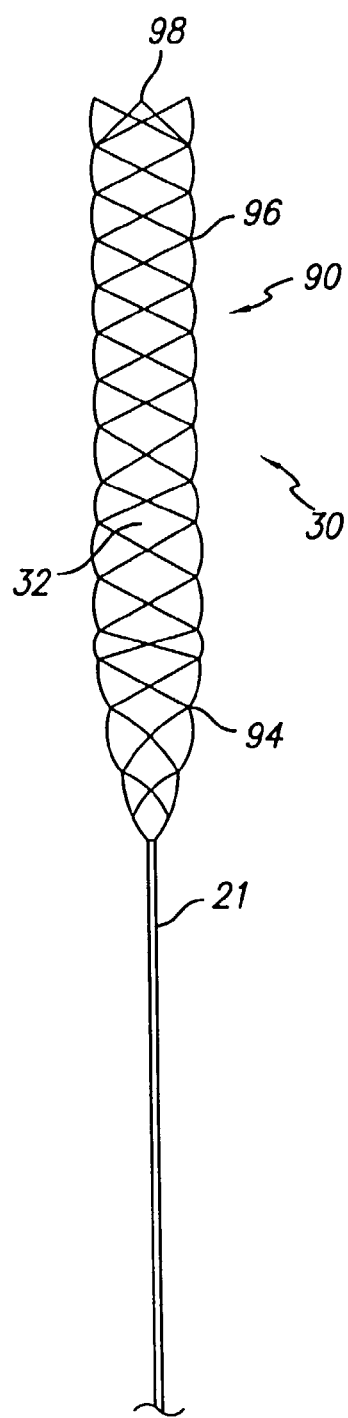
FIG. 7 is a schematic illustration depicting a fourth embodiment of the present invention.

Referring to FIGS. 6 and 7, capture devices 30 employing knitted or mesh structures are shown. Such capture devices, or other suitable devices, can also be used in conjunction with the methods set forth above. Additionally, it may or may not be desirable to treat such devices with thrombogenic material for facilitating formation of fibrin adhesion.

Referring to FIG. 6, a third embodiment of the present invention embodies a knitted or mesh, hollow basket-like capture device 30 that includes basket 82 attached to wire 21. The basket 82 includes a mesh or knitted portion 86 connected by conventional means such as welding via a plurality of proximally extending arms 88 to the distal end of wire 21. The knitted or mesh portion 86 may form a cone-like configuration with its most distal end 89 defining the apex of the cone. It is to be recognized, however, that other basket configurations may also be employed.

Turning to FIG. 7, a fourth embodiment of the present invention includes a hollow knitted or mesh extractor 90 attached to a distal end of wire 21. In this embodiment, the knitted or mesh portion has a cone-like proximal portion 94 that is welded or otherwise affixed to the distal end of wire 21 as well as a generally cylindrical distal portion 96 that extends integrally from the proximal portion 94. The distal end 98 of the knitted or mesh structure terminates at a generally right angle to a longitudinal axis of the knitted or mesh portion and further defines an opening to the hollow interior of the device. This opening may be at least partially closed off in one embodiment.

Figure 8:
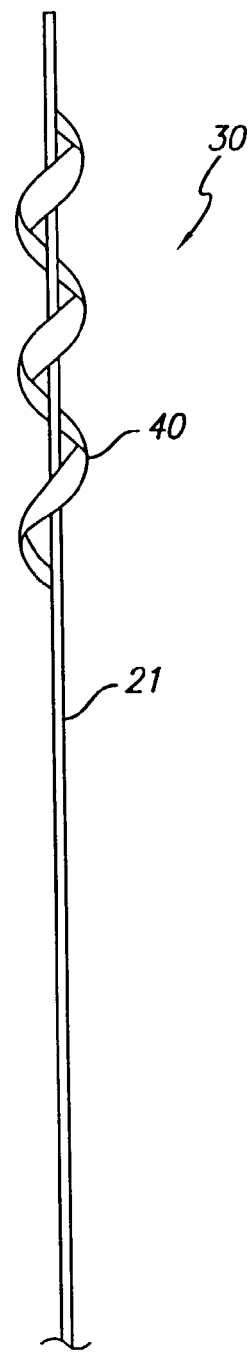
FIG. 8 is a schematic illustration showing a fifth embodiment of the present invention.

Referring now to FIG. 8, in a fifth embodiment of the invention, wire 21 is depicted with capture device 30 as its distal end. The capture device 30 is embodied in ribbon 40 with a helical shape. Consequently, capture device 30 possesses a large amount of surface area. It is contemplated that ribbon 40 may possess other suitable shapes and configurations as well. The ribbon 40 can be self-deploying and capable of assuming an expanded condition and a contracted condition. Alternatively, ribbon 40 can be manually-deployable. The ribbon 40 can be coated with a thrombogenic material to aid the formation of fibrin bonds.

The dimensions and materials referenced herein are by way of example only and not intended to be limiting. For instance, certain dimensions may vary to suit a particular application.

While the invention has been illustrated and described herein in terms of its use a device for the removal of thrombi through physiological adhesion, it will be apparent to those skilled in the art that the invention can be used in other instances. Other modifications and improvements may be made without departing from the scope of the invention.

What is claimed is:

1. A device that removes an obstruction from vasculature, comprising:
   an elongate element having a length sufficient to extend from exterior of a patient's body to a treatment site; and
   a capture device attached to the elongate element, the capture device being coated with a thrombogenic material.

2. The device of claim 1, wherein the capture device can assume an expanded condition and a contracted condition.

3. The device of claim 1, wherein the capture device is self-deploying.

4. The device of claim 1, wherein the capture device includes knitted superelastic wire.

5. The device of claim 1, wherein the capture device includes a mesh-like structure.

6. The device of claim 1, the capture device further comprising a at least one pore formed therein.

7. The device of claim 1, the capture device including a ribbon.

8. The device of claim 7, the ribbon having a helical shape.

9. The capture device of claim 1, the thrombogenic material acting to promote adhesion utilizing blood borne constituents.

* * * * *